(12) United States Patent
Krueger et al.

(10) Patent No.: US 8,847,072 B2
(45) Date of Patent: Sep. 30, 2014

(54) TRANSMISSION CABLE FOR USE IN RADIO-FREQUENCY MAGNETIC OR ELECTRICAL FIELDS

(75) Inventors: Sascha Krueger, Hamburg (DE); Bernd David, Hamburg (DE); Oliver Lips, Hamburg (DE); Steffen Weiss, Hamburg (DE); Daniel Wirtz, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 646 days.

(21) Appl. No.: 12/665,947

(22) PCT Filed: Jun. 27, 2008

(86) PCT No.: PCT/IB2008/052589
§ 371 (c)(1),
(2), (4) Date: Dec. 22, 2009

(87) PCT Pub. No.: WO2009/004548
PCT Pub. Date: Jan. 8, 2009

(65) Prior Publication Data
US 2010/0181109 A1    Jul. 22, 2010

(30) Foreign Application Priority Data
Jun. 29, 2007 (EP) ..................... 07111387

(51) Int. Cl.
| | | |
|---|---|---|
| *H02G 3/00* | (2006.01) | |
| *H01R 4/00* | (2006.01) | |
| *H02G 3/06* | (2006.01) | |
| *H02G 15/08* | (2006.01) | |
| *H01B 7/00* | (2006.01) | |
| *H01B 11/02* | (2006.01) | |
| *H01P 1/10* | (2006.01) | |
| *H01H 1/20* | (2006.01) | |
| *H01H 1/36* | (2006.01) | |
| *G01R 33/28* | (2006.01) | |
| *G01R 33/36* | (2006.01) | |
| *A61B 19/00* | (2006.01) | |
| *A61B 18/00* | (2006.01) | |
| *A61N 1/08* | (2006.01) | |
| *A61B 18/14* | (2006.01) | |

(52) U.S. Cl.
CPC .............. *G01R 33/36* (2013.01); *G01R 33/287* (2013.01); *A61B 2019/5236* (2013.01); *G01R 33/288* (2013.01); *G01R 33/3664* (2013.01); *A61B 2018/00178* (2013.01); *A61N 2001/086* (2013.01); *A61B 18/14* (2013.01)
USPC ........ 174/70 R; 174/85; 174/88 C; 174/88 R; 174/113 R; 174/114 R; 333/105; 200/243; 200/252

(58) Field of Classification Search
USPC ....... 174/70 R, 74 R, 75 C, 75 R, 84 R, 71 C, 174/80, 85, 88 C, 88 R, 113 R, 114 R, 126.1, 174/130, 131 A; 600/423; 333/105; 200/16 A, 16 C, 241, 242, 243, 252, 253
See application file for complete search history.

(56) References Cited

U.S. PATENT DOCUMENTS

| | | | | |
|---|---|---|---|---|
| 2,437,969 | A | * | 3/1948 | Nathan ...................... 174/102 D |
| 4,126,845 | A | * | 11/1978 | Iimori et al. .................. 337/409 |
| 5,458,629 | A | | 10/1995 | Baudino et al. |
| 5,916,162 | A | | 6/1999 | Snelten et al. |
| 6,144,870 | A | | 11/2000 | Griffin, III |
| 6,496,714 | B1 | | 12/2002 | Weiss et al. |
| 6,952,616 | B2 | | 10/2005 | Wessman et al. |
| 6,993,373 | B2 | * | 1/2006 | Vrijheid et al. ............. 174/126.1 |
| 2004/0254450 | A1 | | 12/2004 | Griffin et al. |
| 2006/0142652 | A1 | | 6/2006 | Keenan |
| 2006/0258937 | A1 | | 11/2006 | Daane |

FOREIGN PATENT DOCUMENTS

| | | | | | |
|---|---|---|---|---|---|
| FR | WO 97/33292 | | * | 9/1997 | ............. H01H 15/00 |
| WO | 9949932 | A1 | | 10/1999 | |
| WO | 2004065098 | A1 | | 8/2004 | |
| WO | 2004084748 | A1 | | 10/2004 | |

| | | |
|---|---|---|
| WO | 2004110542 A2 | 12/2004 |
| WO | 2006003566 A1 | 1/2006 |
| WO | 2008015605 A1 | 2/2008 |

OTHER PUBLICATIONS

English machine translation of "CARRIER" provided with Office Action.*

Vernickel, P., et al.; A Safe Transmission Line for MRI; 2005; IEEE Trans. on Biomedical Engineering; 52(6) 1094-1102.

* cited by examiner

*Primary Examiner* — Chau N Nguyen
*Assistant Examiner* — Roshn Varghese (57) ABSTRACT

A transmission cable including a transmission line, at least two electrically conductive line segments separated by a non-conductive gap, a bridging unit including at least one electrically conductive bridge segment capable of bridging the non-conductive gap, and a switching unit arranged to move the bridging unit and/or the transmission line to electrically connect the two line segments by closing the non-conductive gap using the bridge segment or to electrically disconnect the two line segments by opening the non-conductive gap.

13 Claims, 7 Drawing Sheets

TRANSMISSION CABLE FOR USE IN RADIO-FREQUENCY MAGNETIC OR ELECTRICAL FIELDS

FIELD OF THE INVENTION

The invention relates to a transmission cable for use in radio-frequency (RF) electrical and/or magnetic fields, especially in a magnetic resonance (MR) system.

BACKGROUND OF THE INVENTION

The International patent application WO 2004/110542 A2 discusses several alternative designs, materials and methods of manufacturing medical devices such as guidewires, catheters, etc., which may include a plurality of conductive, elongate members connected together. In some embodiments, each adjacent pair of conductive, elongate members is connected in a suitable manner to impede electrical current flow from one elongate member to the next, thus imparting the device a degree of compatibility for use with an MR imaging machine. For example, the elongate members may be connected to each other using a joint having a relatively high electrical resistance or which is relatively non-conductive in relation to the conductive, elongate members.

SUMMARY OF THE INVENTION

It is likely that RF field-induced heating may not occur in case of some MR examinations. However, the embodiments discussed in the above-mentioned prior art document serve to reduce RF field-induced heating in elongate medical devices when they are used in any type of MR examination, by compromising on the electrical transmission capabilities of the medical devices. Thus, there is a need for a transmission cable for use in an elongate medical device such as a catheter, guidewire, etc., wherein the transmission cable is capable of being switched to an MR-safe mode only when necessary, while retaining its optimal electrical transmission properties otherwise.

Accordingly, a transmission cable for use in an RF electrical and/or magnetic field is hereby disclosed. The transmission cable comprises a transmission line including at least two electrically conductive line segments separated by a non-conductive gap, a bridging unit comprising at least one electrically conductive bridge segment capable of bridging the non-conductive gap, and a switching unit arranged to move the bridging unit and/or the transmission line to electrically connect the two line segments by closing the non-conductive gap using the bridge segment or to electrically disconnect the two line segments by opening the non-conductive gap.

The transmission cable disclosed herein may be used in elongate medical devices such as catheters, guidewires, etc. Under circumstances when an MR-safe medical device is required, the switching unit may be operated to disconnect the various line segments forming part of the transmission cable by moving either the transmission line or the bridging unit or both to a relative position such that the non-conductive gap is electrically open. Such a state where the transmission cable is rendered non-transmitting is referred to as "inactive", "passive" or "open" states in this document. In situations when an MR-safe medical device is not required, or when it is required to transmit electrical signals over the transmission cable, the bridging unit and/or the transmission line may be moved to a position such that the bridge segments electrically close the non-conductive gap, thereby restoring the transmission cable with optimal electrical transmission properties. Such a state in which the transmission cable is rendered capable of transmitting electrical signals is also referred to as "active" or "closed" state in this document. Furthermore, the two different states of the transmission cable, i.e., active and passive states, are considered as being electrically complementary to each other.

Furthermore, a method of using a transmission cable as disclosed herein, in a radio-frequency electrical and/or magnetic field is also disclosed, wherein the method comprises operating the switching circuit in order to move the bridging unit and/or the transmission line to electrically connect the two line segments by closing the non-conductive gap using the bridge segment or to electrically disconnect the two line segments by opening the non-conductive gap.

Furthermore, a computer program to perform a method of using a transmission cable as disclosed herein, in a radio-frequency electrical and/or magnetic field is also disclosed, the computer program comprising instructions to operate the switching circuit in order to move the bridging unit and/or the transmission line to electrically connect the two line segments by closing the non-conductive gap using the bridge segment or to electrically disconnect the two line segments by opening the non-conductive gap.

BRIEF DESCRIPTION OF THE DRAWINGS

These and other aspects will be described in detail hereinafter, by way of example, on the basis of the following embodiments, with reference to the accompanying drawings, wherein.

Corresponding reference numerals when used in the various figures represent corresponding elements in the figures.

DETAILED DESCRIPTION OF EMBODIMENTS

Figure 1:
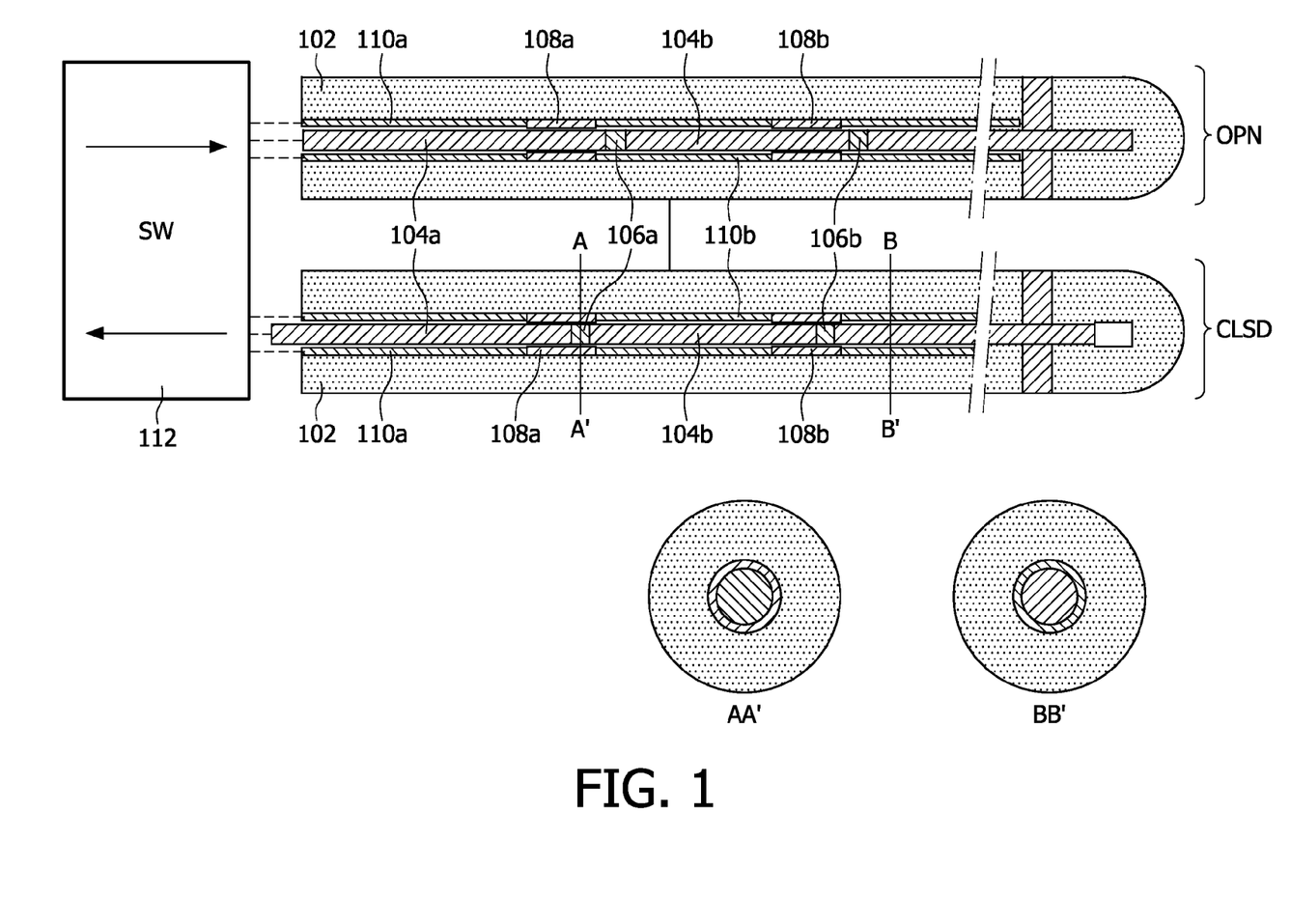
FIG. 1 shows a portion of a catheter incorporating an embodiment of the transmission cable disclosed herein.

FIG. 1 shows a catheter 102 incorporating the transmission cable disclosed herein. The transmission cable includes a transmission line that is divided into a first line segment 104a, a second line segment 104b, and so on, wherein each pair of adjacent line segments is separated by a non-conductive gap 106a, 106b, etc., respectively. The transmission cable also includes a bridging unit that incorporates non-conductive segments 110a, 110b, etc., interspersed with bridge segments 108a, 108b, etc., that are capable of bridging the non-conductive gaps 106a, 106b, etc., respectively. The transmission cable further includes a switching unit (SW) 112 capable of moving either the transmission line or the bridging unit or both. The views AA' and BB' show axial cross-sectional views of the catheter at the locations indicated by the lines A-A' and B-B', respectively, when the transmission cable is in transmitting mode, i.e., when the non-conductive gaps 106a, 106b, etc., are closed by the bridge segments 108a, 108b, etc., respectively. The top panel OPN shows the transmission line and the bridging unit in an open or inactive or passive alignment, i.e., in a configuration that renders the transmission cable RF-safe, while the bottom panel CLSD shows the transmission line and the bridging unit in a closed or active alignment, i.e., in a configuration that renders the transmission cable capable of conducting electricity along its length.

MR-safety of long transmission lines or leads can be achieved by dividing such leads into multiple, short, unconnected sections (or segments). To this end, short sections of non-conducting material are introduced in the transmission line to provide the non-conductive gaps 106a, 106b, etc. Materials that may be used for this purpose include Polyetheretherketone (PEEK), Poyltetrafluorethylene (PTFE), polyester, though other non-conducting or insulating materials in the above-described sense may also be used. As the transmission lead is to be used in an MR environment, it must be borne in mind that the non-conducting materials will also have to be MR-compatible to the desired degree.

The bridging unit forms a complementary conducting structure to the transmission line, as explained below. The transmission line is constructed of relatively long conductive segments 104a, 104b, etc., separated by short non-conductive segments 106a, 106b, etc. The bridging unit, on the other hand, is constructed of relatively long non-conductive segments 110a, 110b, etc., interspersed with short conductive segments or bridge segments 108a, 108b, etc. The bridge segment 108a, 108b, etc., may be made of gold-cladded nitinol; other conducting materials may be used in their construction as well. To make the transmission cable electrically active, the transmission line and the bridging unit are aligned such that a non-conductive gap of the transmission line 106a, 106b etc., is located adjacent to a bridging (conductive) segment 108a, 108b, etc., of the bridging unit and vice versa. When this alignment is disturbed, the transmission cable is rendered inactive or open. Thus, the transmission cable can be made "open" when it is not in use or in case of a safety risk. It may be noted that a "contact failure" does not imply a failure in terms of RF-safety, which is an advantage of this technology when used in conjunction with implantable medical devices such as cardiac pacemakers.

For example, many implantable devices and interventional devices consist of a base unit (not shown) with connected leads or wires that connect the base unit to a remotely located signal transmit/receive unit (not shown). One example of such an interventional device is an MR-compatible catheter for electrophysiological (EP) interventions for mapping (i.e., measurement of local electrocardiogram (ECG) signals), pacing (i.e., local electrical stimulation of myocardium) or ablation (i.e., tissue coagulation and isolation of abnormal electrical pathways). In such a catheter, a "tip electrode" located at the tip of the catheter is connected via a long, coaxial lead to a base unit outside the body. Another example is an MR-compatible catheter for tracking and/or imaging. In this case, in contrast to the aforementioned EP catheter, extremely low-power signals have to be transmitted at MR frequencies. In both of these cases, the transmission cable proposed herein ensures that if a failure occurs due to a loss of contact between the transmission line and the bridging unit, the transmission cable is rendered non-transmitting as well as MR-safe, allowing it to be replaced easily and without danger to the patient. MR-safety can be further enhanced if it is ensured that each of the conducting segments 104a, 104b, etc., of the transmission line and the bridge segments 108a, 108b, etc., are constrained to a length that is less than one quarter of the wavelength of the RF signal being received. However, it may be noted that this is not a necessary limitation for the disclosed transmission cable. The construction of the proposed transmission cable is applicable in a wide variety of applications due to its large frequency bandwidth, low loss and high switching speed.

The switching unit 112 is capable of moving either the transmission line or the bridging unit relative to the other. It may also be possible to move both the transmission line and the bridging unit simultaneously. The switching unit 112 may be operated manually or automatically, using electrical, hydraulic, pneumatic or other actuating means. The movement induced by the switching unit 112 may be a translation, a rotation or a combination of the two. In a simple form, the switching unit 112 may be special handles attached to either the transmission line or the bridging unit or both, that permit the either or both of them to be moved physically by pulling and/or pushing on the handles. By keeping inertia and friction of the transmission line with respect to the bridging unit low (by appropriate choice of materials), high switching rates are possible.

It may be noted that though a cylindrical symmetry is shown for the transmission cable in FIG. 1, other cross-sectional geometries are also considered. A cylindrical symmetry generally assures good electrical contact between the conductive segments of the transmission line and the bridging unit.

FIGS. 2A, 2B, 2C and 2D show alternative embodiments of the disclosed transmission cable implemented in a catheter-like device 102.

Figure 2A:
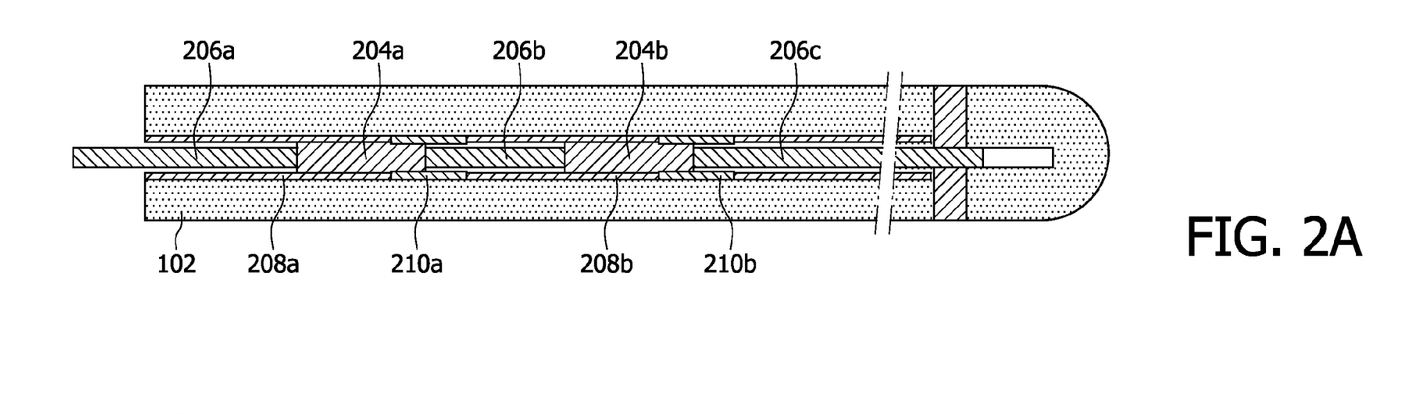
FIG. 2 shows various alternative embodiments of the transmission cable incorporated into an elongate interventional device.

FIG. 2A shows a design of the transmission cable that is configurationally an inverse of the design of FIG. 1. The design includes a transmission line that is divided into a first line segment 204a, a second line segment 204b, and so on, wherein each pair of adjacent line segments is separated by a non-conductive gap 206a, 206b, 206c, etc., respectively. The transmission cable also includes a bridging unit that incorporates non-conductive segments 210a, 210b, etc., interspersed with bridge segments 208a, 208b, etc., that are capable of bridging the non-conductive gaps 206a, 206b, etc., respectively. Unlike in FIG. 1, in the design of FIG. 2A, the transmission line is constructed of relatively short conductive segments 204a, 204b, etc., separated by relatively long non-conductive gaps 206a, 206b, etc. The bridging unit, on the other hand, is constructed of relatively short non-conductive segments 210a, 210b, etc., interspersed with relatively long bridge segments 208a, 208b, etc.

It may be noted that the conductive segments 204a, 204b, etc., may be of different lengths. Similarly, the non-conductive gaps 206a, 206b, etc., the non-conductive segments 210a, 210b, etc., as well as the bridge segments 208a, 208b, etc., may also be of unequal lengths. The transmission line may be made of a central wire made of non-conductive material, coated with a conductive material at the appropriate places to form the line segments 204a, 204b, etc.

Figure 2B:
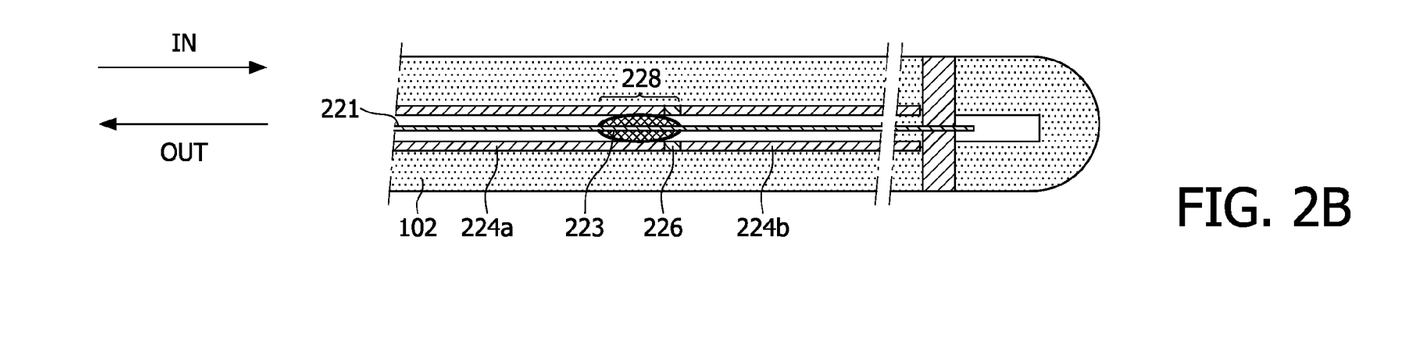

FIG. 2B illustrates a design of the transmission cable utilizing a spring-type contact similar to the brushes (or brush contacts) found in electrical motors, usually for providing a rotatably sliding contact to a rotor shaft. The transmission cable includes a transmission line that is divided into a first line segment 224a and a second line segment 224b separated by a non-conductive gap 226. It is conceivable to have more line segments separated by additional non-conductive gaps as well. The transmission cable also includes a bridging unit 228 that incorporates a spring-type contact 223, which forms the bridge segment in this embodiment. The spring-type contact 223 is mounted on a non-conductive rod element 221, which may be shifted with respect to the transmission line in order to align the spring-type contact 223 with the non-conductive gap 226. When properly aligned, the spring-type contact 223 bridges the non-conductive gap 226 to provide a transmission cable capable of transmitting electrical signals. The advantage of such a construction is that the central non-conductive rod element 221 may be rotated at will, without affecting the electrical connectivity between the line segments 224a, 224b, and thus without affecting the transmission capabilities of the transmission cable.

Figure 2C:
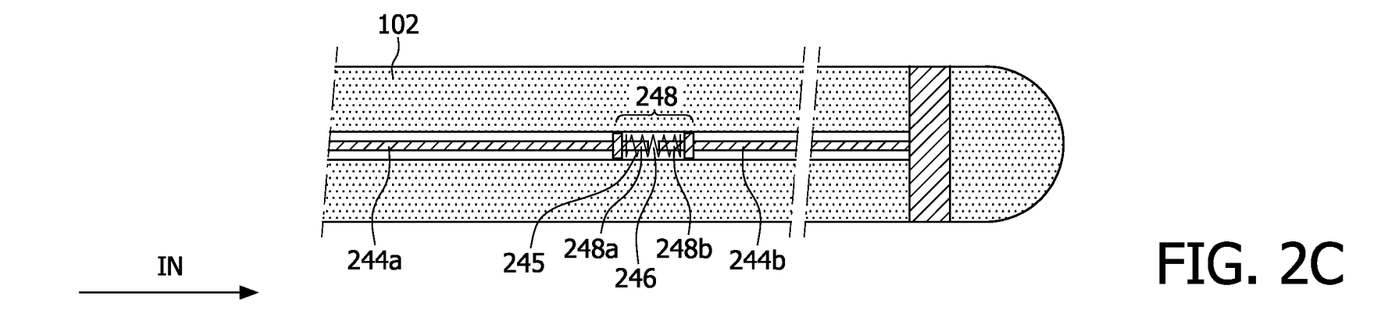

FIG. 2C shows an embodiment of the transmission cable, including a non-conductive spring 245, incorporated into a catheter-like device 102. The transmission cable consists of a transmission line comprising multiple segments, for example, a first line segment 244a, a second line segment 244b, etc. Adjacent line segments 244a, 244b are separated by a non-conductive gap 246. The non-conductive gap could be an air-gap. Alternatively, it is conceivable to use other non-conducting material for the non-conductive gap, for example, oils, gels, inert gases, etc., though adequate sealing may need to be provided to contain the material from leaking. A bridging unit 248 capable of bridging the non-conductive gap 246 consists of a first bridge segment 248a and a second bridge segment 248b. Both the bridge segments are electrically conductive in nature, and are in turn electrically and mechanically connected to the line segment on their respective side. For example, bridge segment 248a is electrically and mechanically connected to line segment 244a, bridge segment 248b is electrically and mechanically connected to line segment 244b, and so on. The bridging unit 248 needs to be activated by applying a force on the line segments 244a, 244b, etc., such that the non-conductive spring 245 is compressed, thereby bringing the two bridge segments 248a, 248b in electrical contact with each other. When the bridging unit 248 is not activated by applying the force, or when the applied force is removed, the bridge segments 248a, 248b stay separated due to the non-conductive spring 245 and the transmission cable remains in a non-conducting and MR-safe state.

In this embodiment, the switching unit (112 of FIG. 1) may be configured to move the transmission line inwards (or in a direction represented by the arrow marked IN) and outwards (or in a direction represented by the arrow marked OUT) with respect to the catheter-like device. When the transmission line is moved inwards, the first line segment 244a moves closer to the second line segment 244b. The first bridge segment 248a, which is substantially rigidly connected to the first line segment 244a, moves closer to the second bridge segment 248b, which is substantially rigidly connected to the second bridge segment 248b, by compressing the spring 245 and closing the non-conductive gap 246. When the two bridge segments 248a, 248b make contact with each other, the transmission cable is rendered capable of transmitting electrical currents. When the switching unit moves the first line segment 244a outwards, or when the applied inward force is removed, the bridging unit 248 is electrically decoupled due to the action of the non-conductive spring 245 acting to push out the two bridge segments 248a, 248b, which renders the transmission cable in a non-transmitting state. Thus, this embodiment has the advantage that the catheter is normally in an MR-safe mode, and becomes electrically active only when the switching unit is activated.

The non-conductive spring 245 may be replaced by alternative non-conductive structures, for example rubber tubes or o-rings, which provide a mechanical force that leads to electrical separation. Using such type of non-conductive mechanical couplers which have some "pulling" tension in the conductive state of the transmission line would result in a corresponding inverse activation-deactivation scheme. In other words, in this possible implementation, the transmission cable would be closed by default and could be opened on demand.

Figure 2D:
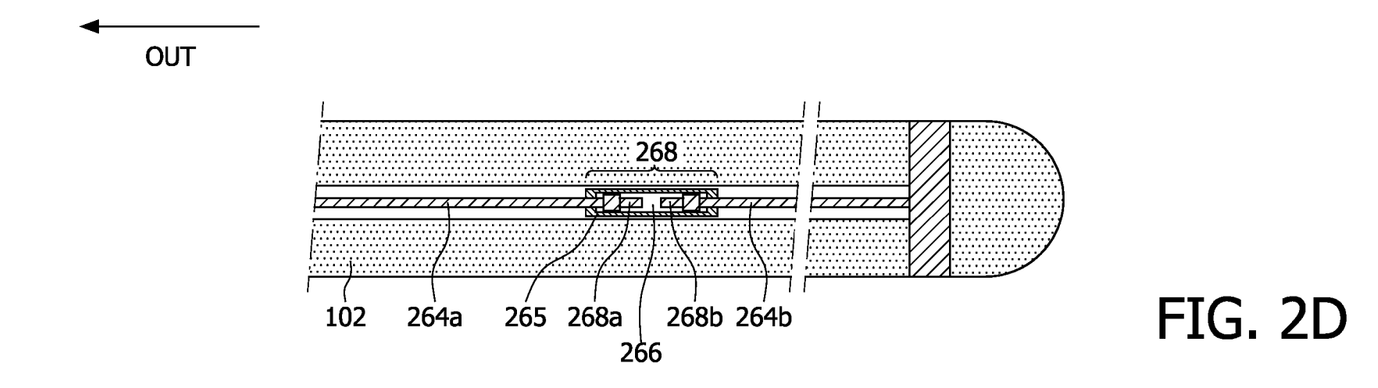

FIG. 2D shows an embodiment of the transmission cable that utilizes a non-conductive mechanical coupler 265, incorporated into a catheter-like device 102. The transmission cable consists of a transmission line comprising multiple segments, for example, a first line segment 264a, a second line segment 264b, etc. Adjacent line segments 264a, 264b are separated by a non-conductive gap 266. The non-conductive gap could be an air-gap. Alternatively, it is conceivable to use other non-conducting material for the non-conductive gap, for example, oils, gels, inert gases, etc., though adequate sealing may need to be provided to contain the material from leaking. A bridging unit 268 capable of bridging the non-conductive gap 266 consists of the non-conductive mechanical coupler 265 consisting of a first bridge segment 268a and a second bridge segment 268b. Both the bridge segments are electrically conductive in nature, and are in turn electrically and mechanically connected to the line segment on their respective side. For example, bridge segment 268a is electrically and mechanically connected to line segment 264a, bridge segment 268b is electrically and mechanically connected to line segment 264b, and so on. The bridging unit 268 needs to be activated or closed by applying a force on the line segments 264a, 264b, etc., such that the non-conductive mechanical coupler 265 is activated, bringing the two bridge segments 268a, 268b in electrical contact with each other. When the bridging unit 268 is not closed, i.e., when the non-conductive gap 266 is not bridged, the bridge segments 268a, 268b stay separated and the transmission cable remains in a non-conducting and MR-safe state.

In this embodiment, the switching unit (112 of FIG. 1) may be configured to move the transmission line inwards (or in a direction represented by the arrow marked IN) and outwards (or in a direction represented by the arrow marked OUT) with respect to the catheter-like device 102. When the transmission line is moved inwards, the first line segment 264a moves closer to the second line segment 264b. The first bridge segment 268a, which is substantially rigidly connected to the first line segment 264a, moves closer to the second bridge segment 268b, which is substantially rigidly connected to the second line segment 264b, thereby closing the non-conductive gap 266 inside the mechanical coupler 265 on contact. When the two bridge segments 268a, 268b make contact with each other, the transmission cable is rendered operational and capable of transmitting electrical currents. When the switching unit moves the first line segment 264a outwards, the electrical connectivity inside the non-conductive mechanical coupler 265 is broken due to the separation of the two bridge segments 268a, 268b inside the bridging unit 268. This renders the transmission cable in a non-transmitting state. Thus, this embodiment has the advantage that the catheter continues either in a conducting state or a non-conducting state until the state is actively changed (to the complementary state) by the operation of the switching unit.

It is to be noted that the transmission cable may be a combination of the various embodiments disclosed herein. It is also to be noted that the directional arrows IN and OUT apply to all the FIGS. 2A, 2B, 2C and 2D.

Figure 3A:
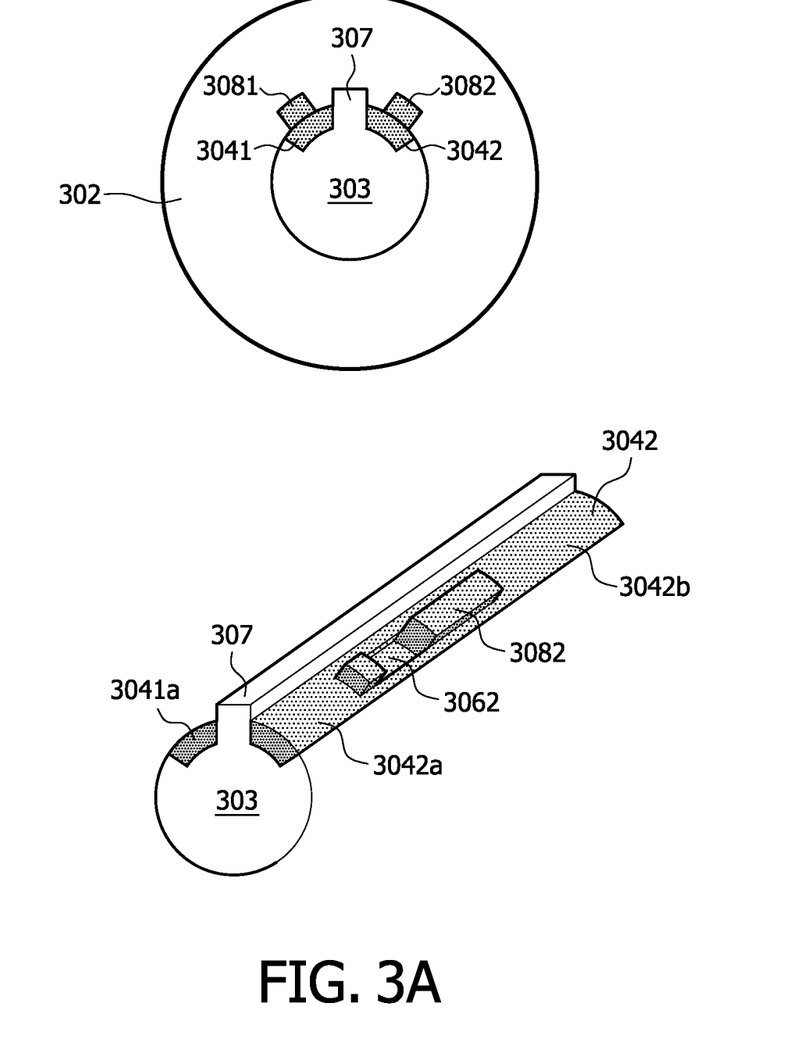
FIG. 3 shows an embodiment of the transmission cable incorporating multiple transmission lines.
Figure 3B:
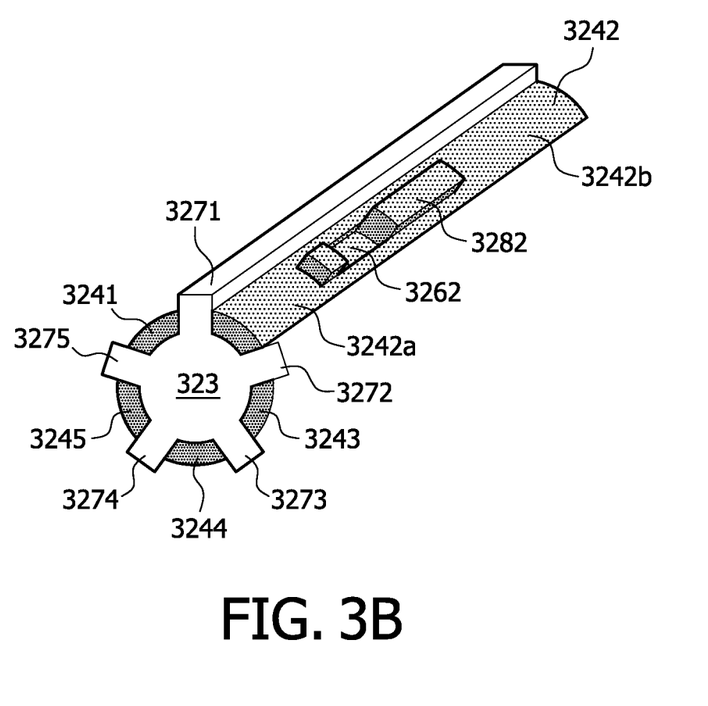
Figure 3C:
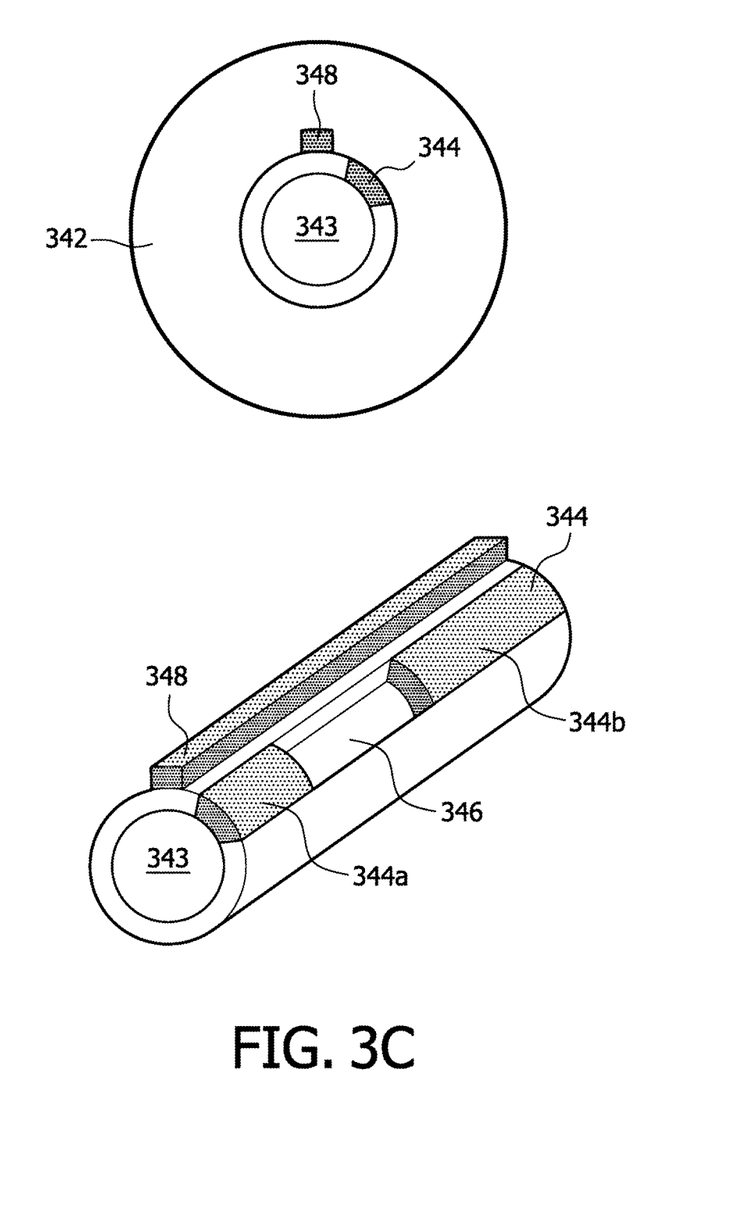

FIGS. 3A and 3B show embodiments of the transmission cable incorporating multiple transmission channels. FIG. 3C shows an embodiment of the transmission cable that utilizes rotatory motion instead of a translatory motion to switch between active and inactive states.

In FIG. 3A, a catheter 302 incorporating an embodiment of the transmission cable having two separate transmission channels is shown. The transmission channels are arranged around a lumen 303 of the catheter 302. A first transmission channel 3042 is made of a transmission line that is split into a first line segment 3042*a* and a second line segment 3042*b* separated by a non-conductive gap 3062, and a first bridge segment 3082. Similarly, a second transmission channel 3041 is made up of a second transmission line that is split into a respective first line segment 3041*a* and second line segment (not shown), separated by a non-conductive gap (not shown), and a second bridge segment 3081. A channel separator 307 provides electrical isolation between the two transmission channels 3041 and 3042.

FIG. 3B extends the concept of the dual-channel transmission cable of FIG. 3A to additional channels. A catheter 322 incorporating an embodiment of the transmission cable that consists of multiple transmission channels arranged around a lumen 323 is shown in the figure. Transmission channels 3241, 3242, 3243, 3244 and 3245 are made up of respective transmission lines that are each split into a first line segment, a second line segment, etc., separated by non-conductive gaps between adjacent line segments. As an example, the transmission line 3242 is made up of a first line segment 3242*a* and a second line segment 3242*b*, separated by a non-conductive gap 3262. The bridge segments 3281, 3282, 3283, 3284 and 3285 are capable of bridging the non-conductive gaps in the respective transmission channels, of which bridge segment 3262 is shown in detail as an example. However, it is to be understood that the other transmission channels are also constructed in a similar fashion and may be operated in a manner similar to transmission channel 3242. Channel separators 3271, 3272, 3273, 3274 and 3275 provide electrical isolation between adjacent transmission channels, as shown in the figure.

The multiple channels may be activated and inactivated simultaneously or independently of each other. A multiple channel transmission cable is advantageous in instances where redundancy of transmission channels is required. Under such a condition, if one transmission channel fails, another transmission channel may be used in its stead. For example, in the case of an implantable device in a patient, in the event of failure of an attached electrical lead, it may normally be necessary to operate on the patient to remove the implanted device, attach a new lead and replace the device inside the patient. However, if a multi-channel transmission cable as disclosed herein is used as the electrical lead, it may be possible to simply switch the transmission channel from a defective one to an operational one, and thereby reduce the necessity of operating on the patient.

Alternatively, the multiple channels may be used simultaneously to transmit different types of information or signals. For example, if a tracking coil (not shown) is attached to the tip of the catheter, then the tracking signals may be transmitted over two transmission channels. Simultaneously, if the catheter also has an RF antenna for ablating tissue, then an RF signal could be transmitted simultaneously over a third transmission channel. The multiple channels may also be operated alternately, in case the operation of one channel is likely to interfere with the operation of another channel.

FIG. 3C shows an embodiment of the transmission cable that utilizes a rotatory mechanism to switch the transmission cable between active and inactive states. A catheter 342, including a lumen 343, incorporates a transmission line 344, which is divided into at least two parts, a first line segment 344*a* and a second line segment 344*b* that are separated by a non-conductive gap 346. A bridge segment 348 is arranged to be rotated into place so as to bridge the non-conducting gap 346, thereby electrically connecting the two line segments 344*a* and 344*b*, and rendering the transmission cable active.

It may be noted that the concept of a rotatory mechanism to switch the transmission cable between active and inactive states may be extended to multi-channel transmission cables similar to the cases described with reference to FIGS. 3A and 3B. The rotatory motion may be imparted manually using a suitable twisting mechanism (not shown) by a switching unit (112 of FIG. 1). Alternatively, the rotatory motion may be automated using stepper motors for higher switching speeds. It is preferable to use MR-compatible mechanical actuators. However, if the mechanical actuator is not MR-compatible, then it could be connected to the transmission cable using MR-compatible Bowden wires, which could be, for example based on glass-fiber reinforced plastic or other artificial materials. Other possibilities to obtain MR-compatible automatic mechanical inputs, such as pneumatic actuators, etc., are also considered. Furthermore, the rotatory mechanism of FIG. 3C may also be spring-loaded such that it is held in one position by default, thereby keeping the transmission cable in an original state (i.e., active or passive). When a force is applied to rotate the transmission line and/or the bridging unit 348 to a position such that the non-conducting gap 346 is closed, the transmission cable is switched to a complementary state (i.e., passive or active, respectively). When the force is removed, the spring-loaded mechanism returns the transmission cable to its original state. Alternatively, the bridging unit 348 may be a mechanical coupler that holds the transmission cable in a particular state (i.e., in a state of inertia) until a force is applied to the mechanical coupler to switch the transmission cable to the complementary state.

Both in the case of the translatory and rotatory mechanisms, the switching between active and inactive (passive) states of the transmission cable may be synchronized to the operation of a connected system, for example, an MR system, as explained with reference to FIG. 4.

Figure 4:
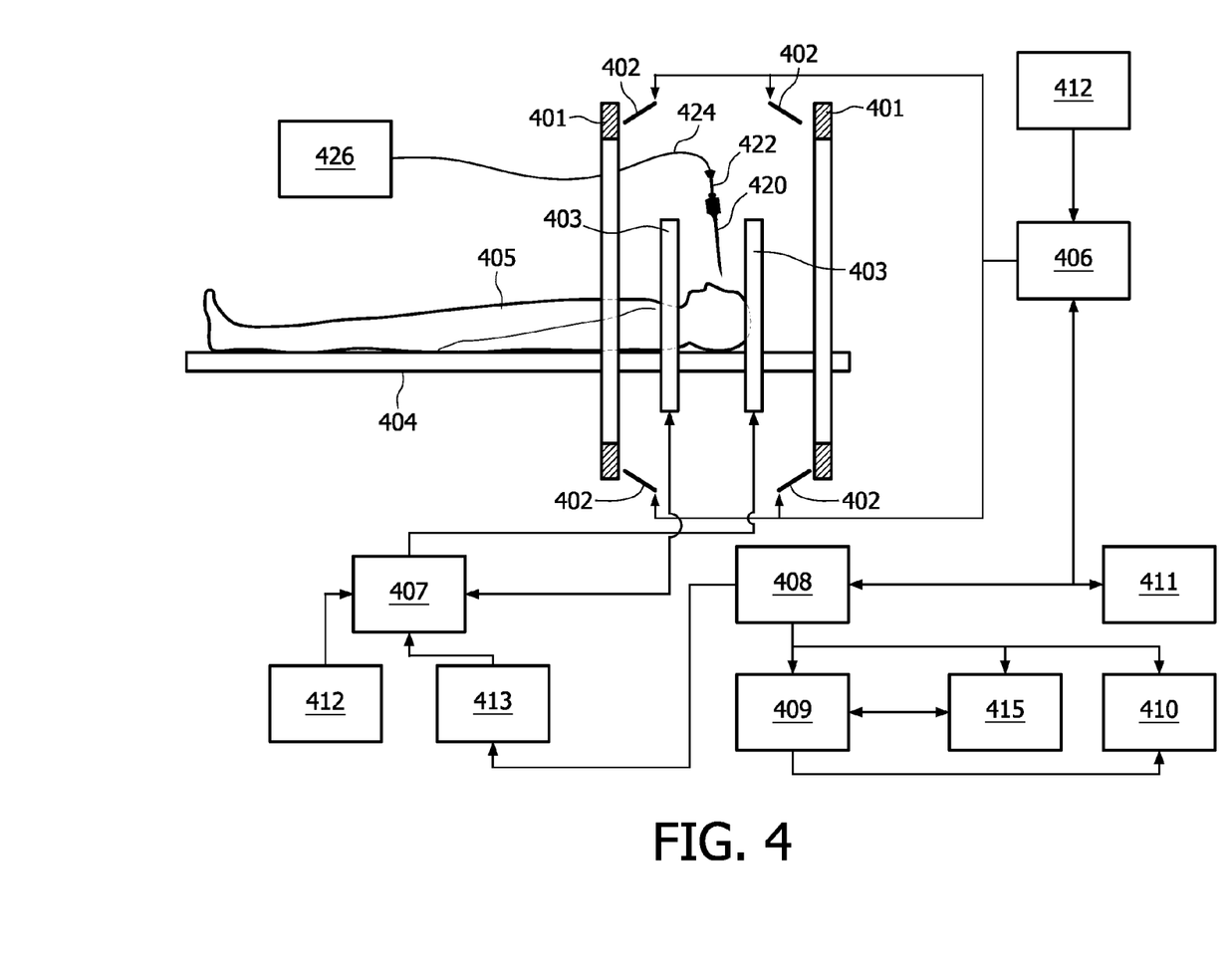
FIG. 4 shows an application of the transmission cable in an MR system.

FIG. 4 shows a possible embodiment of an MR system utilizing the transmission cable disclosed herein. The MR system comprises a set of main coils 401, multiple gradient coils 402 connected to a gradient driver unit 406, and RF coils 403 connected to an RF coil driver unit 407. The function of the RF coils 403, which may be integrated into the magnet in the form of a body coil, or may be separate surface coils, is further controlled by a transmit/receive (T/R) switch 413. The multiple gradient coils 402 and the RF coils are powered by a power supply unit 412. A transport system 404, for example a patient table, is used to position a subject 405, for example a patient, within the MR imaging system. A control unit 408 controls the RF coils 403 and the gradient coils 402. The control unit 408, though shown as a single unit, may be implemented as multiple units as well. The control unit 408 further controls the operation of a reconstruction unit 409. The control unit 408 also controls a display unit 410, for example a monitor screen or a projector, a data storage unit 415, and a user input interface unit 411, for example, a keyboard, a mouse, a trackball, etc. An interventional device 420, for example, an electrode for RF ablation of tissue, is connected to an appropriate power source and/or control system and/or data collection and processing system 426, etc., as necessary, via one or more electrical cables 424. The interventional device 420 incorporates the transmission cable disclosed herein, including a switching unit 422.

The main coils 401 generate a steady and uniform static magnetic field, for example, of field strength 1 T, 1.5 T or 3 T. The disclosed transmission cable may be employed at other field strengths as well. The main coils 401 are arranged in such a way that they typically enclose a tunnel-shaped examination space, into which the subject 405 may be introduced. Another common configuration comprises opposing pole faces with an air gap in between them into which the subject 405 may be introduced by using the transport system 404. To enable MR imaging, temporally variable magnetic field gradients superimposed on the static magnetic field are generated by the multiple gradient coils 402 in response to currents supplied by the gradient driver unit 406. The power supply unit 412, fitted with electronic gradient amplification circuits, supplies currents to the multiple gradient coils 402, as a result of which gradient pulses (also called gradient pulse waveforms) are generated. The control unit 408 controls the characteristics of the currents, notably their strengths, durations and directions, flowing through the gradient coils to create the appropriate gradient waveforms. The RF coils 403 generate RF excitation pulses in the subject 405 and receive MR signals generated by the subject 405 in response to the RF excitation pulses. The RF coil driver unit 407 supplies current to the RF coil 403 to transmit the RF excitation pulse, and amplifies the MR signals received by the RF coil 403. The transmitting and receiving functions of the RF coil 403 or set of RF coils are controlled by the control unit 408 via the T/R switch 413. The T/R switch 413 is provided with electronic circuitry that switches the RF coil 403 between transmit and receive modes, and protects the RF coil 403 and other associated electronic circuitry against breakthrough or other overloads, etc. The characteristics of the transmitted RF excitation pulses, notably their strength and duration, are controlled by the control unit 408.

It is to be noted that though the transmitting and receiving coil are shown as one unit in this embodiment, it is also possible to have separate coils for transmission and reception, respectively. It is further possible to have multiple RF coils 403 for transmitting or receiving or both. The RF coils 403 may be integrated into the magnet in the form of a body coil, or may be separate surface coils. They may have different geometries, for example, a birdcage configuration or a simple loop configuration, etc. The control unit 408 is preferably in the form of a computer that includes a processor, for example a microprocessor. The control unit 408 controls, via the T/R switch 413, the application of RF pulse excitations and the reception of MR signals comprising echoes, free induction decays, etc. User input interface devices 411 like a keyboard, mouse, touch sensitive screen, trackball, etc., enable an operator to interact with the MR system.

The MR signal received with the RF coils 403 contains the actual information concerning the local spin densities in a region of interest of the subject 405 being imaged. The received signals are reconstructed by the reconstruction unit 409, and displayed on the display unit 410 as an MR image or an MR spectrum. It is alternatively possible to store the signal from the reconstruction unit 409 in a storage unit 415, while awaiting further processing. The reconstruction unit 409 is constructed advantageously as a digital image-processing unit that is programmed to derive the MR signals received from the RF coils 403.

The interventional device 420, for example, a catheter or guidewire, an EP catheter, an RF-ablation catheter or needle-electrode, etc., is connected to additional systems as required, as shown by the box 426. For example, the interventional device 420 may be connected to an interventional control system 426 that is capable of switching the transmission cable incorporated into the interventional device 420, between active and passive states. The switching may be based on measurement of tissue temperature at the tip of the interventional device 420. Alternatively, it may be based on measurement of the time duration and strength of RF power that is being deposited by an RF-ablation needle into the tissue. By taking into account the local tissue absorption properties and heat transport effects, it may be possible to predict when the transmission cable would cross a safe "therapeutic" limit for the RF-heating, and induce unwanted or "non-therapeutic" RF-heating, at which point it could be switched to a passive state. Alternatively, the coupling of an MR transmit RF coil 403 to the lead 424 of the interventional device 420 could be monitored by continuously measuring the strength of the RF-signal transmitted by the RF coil 403 during MR imaging. This could, for example, be monitored by internal (additional) receive coils (not shown) of the MR system (normally, such additional coils are used for coil-tuning and other preparatory measurements). In either case, the local SAR as estimated from an absorption measurement could then be used as a safety criterion. In case the temperature, SAR, or other important measured factor rises above a prescribed threshold, the transmission cable is deactivated and thus made safe for the patient. The temperature measurement can be performed using MR-safe fiber-optic techniques. It may be noted that the interventional control system 426 to control the interventional device 420 may be combined with or may otherwise form part of the control unit 408. The switching unit 422 may be a handle that is activated manually to push and/or pull parts of the transmission cable, as explained earlier. Alternatively, the switching unit 422 may be a mechanical device that is capable of automatically moving the transmission line and/or the bridging unit to activate or deactivate the transmission cable. An example of such a device is the stepper motor device mentioned with reference to FIG. 3C. Other examples include actuators that can impart a linear motion to the required parts of the transmission cable, as explained earlier. Though the switching unit 422 is shown attached to the interventional device 420, it could be alternatively located at a remote location, and connected to the interventional device via mechanical, electrical, pneumatic, hydraulic, etc., mechanisms.

In another possible embodiment, the interventional control system 426 is connected to the MR control unit 408 (the connection is not explicitly shown in the figure). The MR system, via the control unit 408, triggers the interventional control system 426 to deactivate the transmission cable during RF transmission, for example, when an MR pulse sequence is being played out. This could be useful in MR-guided interventional EP procedures, wherein the EP catheter is guided using realtime MR imaging, thus enabling a simultaneous trans-catheter diagnosis and therapy combined with MR imaging. Alternatively, the state of the transmission cable may be monitored by the interventional control system 426 and communicated to the MR system via the control unit 408. For example, during mapping, pacing or ablation procedures using the EP catheter, the transmission cable has to be in an active or "transmitting" state. This state could be sensed by the MR control unit 408, via the interventional control system 426, and the transmission of RF power by the MR system could be automatically prohibited or weakened during this period. A highly resistive wire or any other MR-safe way may be used to monitor the impedance of the transmission cable.

The use of existing transmission cables is generally restricted to a particular frequency and/or power range. Furthermore, generally during use, the electrical transmission capabilities of existing transmission cables are compromised compared to a standard transmission line. In contrast, the disclosed transmission cable allows RF signal and power transmission over a large bandwidth of frequencies, making it suitable for use in tracking, imaging and other diagnostic and therapeutic applications, without compromising its electrical transmission properties. In particular, the disclosed transmission cable allows transmission of RF signals at frequencies ranging from zero (i.e., direct current or DC) to high frequencies that can be transmitted via transmission lines, at a wide range of power levels within the therapeutically useful domain. It is also useful to note that, in contrast to interventional devices incorporating other types of RF-safe transmission lines, the mechanical properties of an interventional device (which properties are key for its clinical usefulness) incorporating the transmission cable disclosed herein are only minimally altered due to the small diameters of the transmission cable achievable in the disclosed designs.

The control unit 408 is capable of loading and running a computer program comprising instructions that, when executed on the computer, enables the computer to execute the various aspects of the methods disclosed herein. The computer program disclosed herein may reside on a computer readable medium, for example a CD-ROM, a DVD, a floppy disk, a memory stick, a magnetic tape, or any other tangible medium that is readable by the computer. The computer program may also be a downloadable program that is downloaded, or otherwise transferred to the computer, for example via the Internet. The transfer means may be an optical drive, a magnetic tape drive, a floppy drive, a USB or other computer port, an Ethernet port, WLAN or other wireless technologies, etc.

It is to be noted that throughout this document, the word "conductive" indicates a low electrical impedance at a particular signal frequency, while the word "non-conductive" indicates a high electrical impedance at the particular signal frequency. A low electrical impedance allows transmission of electrical signal, while a high impedance provides RF-safety depending on the type of application or situation. Thus, neither of the terms "conductive" or "non-conductive" is limited to certain impedance ranges. The disclosed transmission cable is furthermore not restricted to a certain frequency range but may be operated at signal frequencies ranging from 0 Hz (DC) to the highest alternating current (AC) frequencies, which may be transferred via a transmission line. The disclosed transmission cable also relates to any kind of signal propagation mode, common and differential mode being named as examples here. The disclosed transmission cable extends to arbitrary signal powers and is meant for either transmission or reception of signals or both.

The order in the described embodiments of the disclosed methods is not mandatory. A person skilled in the art may change the order of steps or perform steps concurrently using threading models, multi-processor systems or multiple processes without departing from the disclosed concepts.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The disclosed method can be implemented by means of hardware comprising several distinct elements, and by means of a suitably programmed computer. In the system claims enumerating several means, several of these means can be embodied by one and the same item of computer readable software or hardware. The mere fact that certain measures are recited in mutually different dependent claims does not indicate that a combination of these measures cannot be used to advantage.

The invention claimed is:

1. A transmission cable for use in a radio-frequency electrical and/or magnetic field, comprising:
    a transmission line including a plurality of electrically conductive line segments and at least one non-conductive partition formed from non-conductive material separating adjacent line segments;
    a bridging unit comprising a non-conductive segment and at least one electrically conductive bridge segment for bridging the adjacent line segments over the at least one non-conductive partition; and
    a switching unit arranged to move the bridging unit and/or the transmission line with respect to each other, the non-conductive segment and the at least one electrically conductive bridge segment together moving axially relative to the transmission line
        to electrically connect the adjacent line segments by bridging each non-conductive partition with the bridge segments, and
        to electrically disconnect the adjacent line segments by removing the bridge segments over the non-conductive partition.

2. The transmission cable as claimed in claim 1, wherein the bridging unit includes a spring-type brush contact mounted on a non-conductive rod, and the switching unit is configured to close the non-conductive partition using the spring-type brush contact, by translating the non-conductive rod.

3. The transmission cable as claimed in claim 1, wherein the bridging unit includes a non-conductive spring configured to keep the non-conductive partition open, and the switching unit is configured to close the non-conductive partition by applying a force on the non-conductive spring.

4. The transmission cable as claimed in claim 1, wherein the bridging unit includes a mechanical coupling element configured to keep the transmission cable in an original electrical state until switched to a complementary electrical state by the switching unit.

5. The transmission cable as claimed in claim 1, wherein the switching unit is configured to translate the bridging unit and/or the transmission line.

6. The transmission cable as claimed in claim 1, wherein the switching unit is configured to rotate the bridging unit and/or the transmission line.

7. The transmission cable of claim 1, wherein the cable is incorporated in an interventional device.

8. The transmission cable as claimed in claim 7, wherein the interventional device is included in a magnetic resonance system.

9. The transmission cable as claimed in claim 1, wherein the axial movement includes at least one of rotational movement and translational movement.

10. A method of using a transmission cable in a radio-frequency electrical and/or magnetic field, the method comprising acts of:
    using the transmission cable having
        a transmission line including a plurality of electrically conductive line segments and at least one non-conductive partition formed from non-conductive material separating adjacent line segments,
        a bridging unit comprising a non-conductive segment and at least one electrically conductive bridge segment for bridging the adjacent line segments over the at least one non-conductive partition, and
        a switching unit arranged to move the bridging unit and/or the transmission line with respect to each other to electrically connect the adjacent line segments by bridging each non-conductive partition with the bridge segments and to electrically disconnect the adjacent line segments by removing the bridge segments over the non-conductive partition, the non-conductive segment and the at least one electrically conductive bridge segment together moving axially relative to the transmission line; and operating the switching unit to move the bridging unit and/or the transmission line to electrically connect the plurality of line segments by closing the non-conductive partition using the bridge segment or to electrically disconnect the two line segments by opening the non-conductive partition.

11. The method as claimed in claim 10, wherein the axial movement includes at least one of rotational movement and translational movement.

12. A computer readable non-transitory medium comprising a program that when executed by a computer performs a method of using a transmission cable in a radio-frequency electrical and/or magnetic field, the computer program comprising instructions to perform acts of:

using the transmission cable having
- a transmission line including a plurality of electrically conductive line segments and at least one non-conductive partition formed from non-conductive material separating adjacent line segments,
- a bridging unit comprising a non-conductive segment and at least one electrically conductive bridge segment for bridging the adjacent line segments over the at least one non-conductive partition, and
- a switching unit arranged to move the bridging unit and/or the transmission line with respect to each other to electrically connect the adjacent line segments by bridging each non-conductive partition with the bridge segments and to electrically disconnect the adjacent line segments by removing the bridge segments over the non-conductive partition, the non-conductive segment and the at least one electrically conductive bridge segment together moving axially relative to the transmission line; and operating the switching unit to move the bridging unit and/or the transmission line to electrically connect the plurality of line segments by closing the non-conductive partition using the bridge segment or to electrically disconnect the two line segments by opening the non-conductive partition.

13. The medium as claimed in claim 12, wherein the axial movement includes at least one of rotational movement and translational movement.

* * * * *